United States Patent [19]
Reed

[11] Patent Number: 5,633,351
[45] Date of Patent: May 27, 1997

[54] TARGETING PROTEIN-DIAGNOSTIC/ THERAPEUTIC AGENT CONJUGATES HAVING SCHIFF BASE LINKAGES

[75] Inventor: Michael W. Reed, Seattle, Wash.

[73] Assignee: NeoRx Corporation, Seattle, Wash.

[21] Appl. No.: 332,045

[22] Filed: Nov. 1, 1994

Related U.S. Application Data

[63] Continuation of Ser. No. 13,484, Feb. 1, 1993, abandoned, which is a continuation of Ser. No. 621,709, Dec. 4, 1990, abandoned, which is a division of Ser. No. 252,298, Sep. 30, 1988, abandoned.

[51] Int. Cl.$^6$ .................... A61K 51/00; C07K 16/00
[52] U.S. Cl. .................... 530/391.1; 530/391.3; 530/391.5; 530/391.9; 424/9.34
[58] Field of Search ............... 530/391.1, 391.3, 530/391.5, 391.9; 424/1.49, 1.53, 179.1, 9.34

[56] References Cited

U.S. PATENT DOCUMENTS

| | | | |
|---|---|---|---|
| 3,959,080 | 5/1976 | Orth et al. | 195/63 |
| 4,093,607 | 6/1978 | Sela et al. | 260/112 B |
| 4,153,417 | 5/1979 | Hällgren et al. | 23/23 B |
| 4,314,987 | 2/1982 | Morris et al. | 424/1 |
| 4,443,426 | 4/1984 | Thakur | 424/1.1 |
| 4,634,586 | 1/1987 | Goodwin et al. | 424/1.1 |
| 4,671,958 | 6/1987 | Rodwell et al. | |
| 4,735,792 | 4/1988 | Srivastava | 424/1.1 |
| 4,801,688 | 1/1989 | Laguzza et al. | |
| 4,867,973 | 9/1989 | Goers et al. | 424/85.91 |
| 4,868,106 | 9/1989 | Ito et al. | 435/7 |
| 4,925,648 | 5/1990 | Hansen et al. | 424/1.1 |
| 4,950,738 | 8/1990 | King et al. | 530/322 |
| 5,057,302 | 10/1991 | Johnson et al. | 424/1.1 |
| 5,066,789 | 11/1991 | Srinivasan et al. | 530/388 |

FOREIGN PATENT DOCUMENTS

| | | |
|---|---|---|
| 0 175 617 | 3/1986 | European Pat. Off. . |
| 0 188 256 | 7/1986 | European Pat. Off. . |
| 0 203 764 | 12/1986 | European Pat. Off. . |
| 0 328 147 | 8/1989 | European Pat. Off. . |
| 87/06837 | 5/1987 | WIPO . |
| 88/02594 | 10/1987 | WIPO . |

OTHER PUBLICATIONS

Zwierina, Stem Cells, 11:144, 1993.

Jain, Sci. Amer., 271:58, 1994.

Curti, Clin. Rev. Oncol/Hematol., 14:29, 1993.

Parker (ed.), Radioimmunoassay of Biologically Active Compounds, Prentice–Hall, Inc., Englewood Cliffs, New Jersey, p. 93.

Van Vunakis et al. (eds.), Methods in Enzymology, vol. 70, Immunochemical Techniques, Academic Press, New York, 1980, p. 101.

King et al., "Preparation of Protein Conjugates via Intermolecular Hydrazone Linkage," biochemistry 1986, 25, 5774–5779.

Seventy–Ninth Annual Meeting of the American Association for Cancer Research, May 25–28, 1988, Proceedings, New Orleans, vol. 29, Mar. 1988, p. 288.

Kravolec et al., "Synthesis of site–specific methotrexate–IgG conjugates," Cancer Immunol. Immunoether (1989) 29:293–302.

Primary Examiner—Frank C. Eisenschenk
Attorney, Agent, or Firm—Burns, Doane, Swecker & Mathis, L.L.P.

[57] ABSTRACT

Targeting protein-diagnostic/therapeutic agent conjugates joined by stabilized Schiff base linkages are disclosed. Schiff base linkage of targeting protein and agent is accomplished without exposure of the targeting protein to harsh oxidizing or reducing conditions. The cleavable, heterobifunctional linkers that are described provide certain advantages relating to in vivo administration of targeting protein conjugates, including controlled release of active agent at a target site.

7 Claims, No Drawings

TARGETING PROTEIN-DIAGNOSTIC/THERAPEUTIC AGENT CONJUGATES HAVING SCHIFF BASE LINKAGES

This application is a continuation of application Ser. No. 08/013,484, filed Feb. 1, 1993, now abandoned, which is in turn a continuation of Ser. No. 07/621,709, filed Dec. 4, 1990, now abandoned, which is in turn a divisional of Ser. No. 07/252,298, filed Sep. 30, 1988, now abandoned.

TECHNICAL FIELD

The claimed invention relates to targeting protein-diagnostic/therapeutic agent conjugates that are joined by an improved Schiff base linkage that provides advantageous properties for in vivo imaging and therapy.

BACKGROUND OF THE INVENTION

A Schiff base is an imine condensation product of an aldehyde and a primary amine. Formation of a Schiff base may be illustrated by the following reaction:

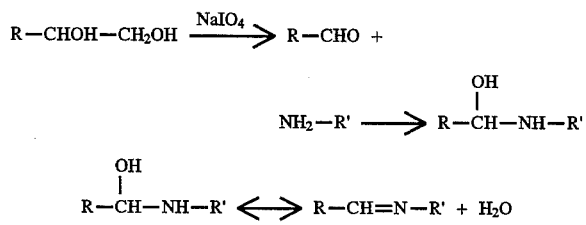

Where R and/or R' are aliphatic substituents, the C=N (imine) bond of a Schiff base is known to be very unstable. Typically, the C=N bond is stabilized by reduction with sodium borohydride or sodium cyanoborohydride, as represented by the following reaction:

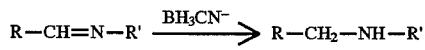

Stabilization of the C=N bond may also be achieved through the attachment of an aryl(s) to the imine carbon or nitrogen, or if a hydroxyl or second nitrogen is bonded to the imine nitrogen.

Schiff base linkages have been used for conjugation of glycoproteins in general, and for conjugation of immunoglobulins in particular. In a typical reaction scheme, oligosaccharide moieties present on an immunoglobulin molecule are oxidized to form one or more aldehyde groups. The resultant immunoglobulin aldehyde(s) is reacted with a primary amine to form a Schiff base, which is then stabilized by reduction.

A prototypical Schiff base conjugation procedure (as described above) suffers from numerous disadvantages. First, the immunoglobulin (glycoprotein) molecule is subjected to very harsh oxidizing conditions in order to generate free aldehyde groups. This harsh oxidation may result in impairment of the biological activity of the immunoglobulin molecule. Second, stabilization of the Schiff base conjugate is accomplished through exposure of the conjugate to a harsh reducing agent, which also may adversely affect the biological function of the immunoglobulin moiety. Third, the number of substituents that may be conjugated by Schiff base linkage to immunoglobulin aldehyde groups is limited by the number of carbohydrate moieties present on a particular immunoglobulin molecule. For instance, the amount of carbohydrate present on an immunoglobulin molecule may vary between 2–3% for IgG and 9–12% for IgM, IgD and IgE (I. M. Roitt et al, "Immunology", Gower Medical Publishing Ltd., 1985, p. 5.2).

Alternatively, an aldehyde generated on an immunoglobulin molecule may be reacted with a hydrazide to form a hydrazone, according to the following reaction scheme:

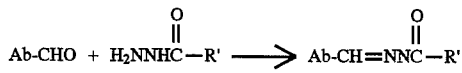

Hydrazones are more stable than Schiff bases formed by the reaction of an aldehyde and a primary amine, and thus do not require reduction after formation of the linking bond. However, this reaction scheme suffers from several disadvantages: (1) the immunoglobulin must still be oxidized to generate free aldehyde groups; and (2) the degree of conjugation is limited by the number of carbohydrate moieties present on the immunoglobulin molecule.

SUMMARY OF THE INVENTION

The present invention provides targeting protein conjugates covalently bonded to one or more diagnostic or therapeutic agents through improved Schiff base linkages. Oxidation/reduction of the targeting protein component is eliminated; a variety of targeting protein substituents may be used to produce a Schiff base-linked conjugate.

Targeting protein-diagnostic/therapeutic agent conjugates joined by an aromatic, heterobifunctional Schiff base linker are also disclosed. In one embodiment, the Schiff base linkage is formed between the targeting protein and the linker. In a second embodiment, the Schiff base linkage is formed between the agent and the linker. The latter linker may further provide enhanced target cell retention of the conjugate.

DETAILED DESCRIPTION OF THE INVENTION

Prior to setting forth the invention, it may be helpful to set forth definitions of certain terms to be used within the disclosure.

Schiff base linkage: A chemical bond represented by R—CH=NH—R'.

Stabilized Schiff base linkage: A chemical bond represented by R—CH=NNHCOR' (hydrazone).

Conventional Schiff base linkage: A Schiff base linkage formed by reaction of an aldehyde or ketone group present on a targeting protein with a nucleophilic primary amine or hydrazide present on a diagnostic or therapeutic agent.

Unique Schiff base linkage: A Schiff base linkage formed by reaction of a primary amine or hydrazide present on a targeting protein with an aldehyde or ketone present on a diagnostic or therapeutic agent.

Targeting protein: A protein or peptide that binds to a defined population of cells. The targeting protein or peptide may bind a receptor, an enzymatic substrate, an antigenic determinant, or other binding site present on the target cell population. Hereinafter, the term "targeting protein" will be inclusive of both targeting proteins and targeting peptides.

Conjugate: A two-component hybrid molecule wherein the components are joined by a covalent chemical linkage.

Targeting protein conjugate: A conjugate wherein one component is antibody (i.e., an immunoconjugate) or, more generally, a targeting protein. Typically, the second component of a targeting protein conjugate is a therapeutic agent (i.e., a drug, a toxin or a radionuclide) or a diagnostic agent (i.e., a radionuclide).

A first aspect of the present invention describes a conjugate of a targeting protein and a diagnostic or therapeutic agent covalently joined through one or more stabilized Schiff base linkages.

In a first aspect of the claimed invention, a targeting protein conjugate is joined through a stabilized unique Schiff base linkage, as represented below:

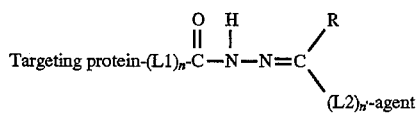

wherein
"Tp" is a targeting protein (such as a peptide, polypeptide, glycoprotein, carbohydrate-free protein, targeting protein, carrier protein or chelator);
"L1" and "L2" are heterobifunctional linkers having a hydrazide or aldehyde/ketone active group at one end of the linker;
"n" and "n'" are 0 or 1;
"R" is H; an alkyl, aryl, or alicyclic substituent; and
"agent" is a diagnostic or therapeutic agent useful for in vivo applications, or a chelating agent capable of binding small diagnostic or therapeutic molecules.

Preferred targeting proteins useful within the present invention include antibody and antibody fragments; peptides, such as bombesin, gastrin-releasing peptide, RGD peptide, substance P, neuromedin-B, neuromedin-C, and metenkephalin; and hormones, such as EGF, $\alpha$- and $\beta$-TGF, estradiol, neurotensin, melanocyte stimulating hormone, follicle stimulating hormone, luteinizing hormone, and human growth hormone. Biotin, avidin, proteins corresponding to known cell surface receptors (including low density lipoproteins, transferrin, insulin and $CD_4$), fibrinolytic enzymes, and biological response modifiers (including interleukin, interferon, erythropoietin and colony-stimulating factor) are also preferred targeting proteins. Analogs of the above-listed targeting proteins that retain the capacity to bind to a defined target cell population may also be used within the claimed invention. In addition, synthetic targeting proteins and peptides may be designed.

Exemplary cytotoxic agents include toxins and drugs. Several of the native toxins useful within the present invention consist of an A and a B chain. The A chain is the cytotoxic portion and the B chain is the receptor-binding portion of the intact toxin molecule (holotoxin). Because toxin B chain may mediate non-target cell binding, it is often advantageous to conjugate only the toxin A chain to a targeting protein. However, while elimination of the toxin B chain decreases non-specific cytotoxicity, it also generally leads to decreased potency of the toxin A chain-targeting protein conjugate, as compared to the corresponding holotoxin-targeting protein conjugate.

One possible explanation for the decreased potency of A chain-targeting protein conjugates is that B chain is required for translocation of the A chain across endosomic membranes into the target cell cytoplasm. In the absence of translocation, the targeting protein conjugate remains in the interior of an endosome, and is ultimately transported to a lysosome. Within the lysosome, the targeting protein conjugate is degraded, and thus the A chain cytotoxic agent fails to reach its cytoplasmic target site. The decreased potency associated with toxin A chain-targeting protein conjugates also accompanies the use of ribosomal inactivating protein-targeting protein conjugates. Ribosomal inactivating proteins (RIPs) are naturally occurring protein synthesis inhibitors that lack translocating and cell-binding ability.

Within the present invention, preferred toxins include holotoxins, such as abrin, ricin, modeccin, Pseudomonas exotoxin A, Diphtheria toxin, pertussis toxin and Shiga toxin; and A chain or "A chain-like" molecules, such as ricin A chain, abrin A chain, modeccin A chain, the enzymatic portion of Pseudomonas exotoxin A, Diphtheria toxin A chain, the enzymatic portion of pertussis toxin, the enzymatic portion of Shiga toxin, gelonin, pokeweed antiviral protein, saporin, tritin, barley toxin and snake venom peptides.

Exemplary drugs include daunomycin, adriamycin, vinblastine, doxorubicin, bleomycin, methotrexate, 5-fluorouracil, 6-thioguanine, cytarabine, cyclophosphamide and similar conventional chemotherapeutics as described in *Cancer: Principles and Practice of Oncology*, 2d ed., V. T. DeVita, Jr., S. Hellman, S. A. Rosenberg, J. B. Lippincott Co., Philadelphia, Pa., 1985, Chapter 14. Yet another preferred drug within the present invention belongs to the trichothecene family, with verrucarin A particularly preferred. Experimental drugs may also be suitable for use within the present invention (see, e.g., *NCI Investigational Drugs, Pharmaceutical Data* 1987, NIH Publication No. 88-2141, Revised November 1987).

Conjugates of targeting proteins and cytotoxic agents joined through non-stabilized unique Schiff base linkages have been described (Sela et al., U.S. Pat. Nos. 4,093,607 and 4,263,279). Such unique Schiff base conjugates may be represented by the following formula:

$$\text{Protein-NH=CH-cytotoxic agent}$$

which upon reduction yields:

$$\text{Protein-NH—CH}_2\text{-cytotoxic agent.}$$

A stabilized unique Schiff base-linked targeting protein conjugate of the present invention, as described above, provides certain advantages as compared to previously described non-stabilized, reduced unique Schiff base conjugates:

(1) Various substituents of the targeting protein may be used to produce a stabilized unique Schiff baselinked conjugate of the claimed invention. For instance, a native disulfide bond within the targeting protein may be used to generate a free sulfhydryl, which in turn reacts with a maleimide end of a heterobifunctional linker having a hydrazide or aldehyde group present at the other end of the linker molecule. If the targeting protein does not possess a native disulfide bond, lysine residues may be used to introduce free sulfhydryl groups into the targeting protein through reaction with iminothiolane. In yet another embodiment of the invention, targeting protein carboxylic acid groups may be reacted with hydrazine to form a targeting protein hydrazide. Thus, either sulfhydryls, lysines or carboxylic acid groups of a targeting protein may be used for production of unique Schiff base-linked targeting protein conjugates described herein.

In contrast, a non-stabilized unique Schiff base linkage according to Sela et al. requires binding of periodate-oxidized drug to free amino groups of protein to form a non-stabilized imine linkage.

(2) Formation of a stabilized unique Schiff base (hydrazone) linkage according to the present invention does not require reduction of the resultant conjugate for stabilization. The non-stabilized unique Schiff base (imine) conjugate schematically represented above must be reduced with sodium borohydride or sodium cyanoboro-hydride for stabilization of the imine bond. Reduction of the imine bond to an amine bond makes the linkage non-cleavable under biologic conditions. In addition to reduction of the imine bond to an amine bond, exposure to borohydride or cyanoborohydride may also reduce disulfide bonds and amide linkages, and produce other as yet unidentified deleterious effects on the protein and cytotoxic agent components of the conjugate.

In one embodiment of this aspect of the invention, lysine groups of a targeting protein (either glycoprotein or non-glycoprotein) are treated with a reagent (for instance, iminothiolane) that adds free sulfhydryl groups to the targeting protein. The sulfhydryl-derivatized targeting protein (Tp-SH) is then reacted with a heterobifunctional linker having a maleimide reactive group.

An exemplary heterobifunctional linker in this regard has a maleimide reactive group at one end and a hydrazide reactive group at the other end. One example of a heterobifunctional linker useful in this regard is:

$$H_2N-HN-\underset{\underset{O}{\|}}{C}-\text{C}_6\text{H}_4-CH_2-N\begin{pmatrix}\text{maleimide}\end{pmatrix} \quad \text{Formula 1}$$

which may be obtained by the following reaction scheme:

$$\text{NHS-O-C(=O)-C}_6\text{H}_4\text{-CH}_2\text{-N(maleimide)} + NH_2NH_2 \longrightarrow H_2N-HN-C(=O)-C_6H_4-CH_2-N(\text{maleimide})$$

Alternatively, the maleimide group of the described heterobifunctional linker may be reacted with native sulfhydryl groups on the targeting protein. Native sulhydryls may be generated from targeting protein disulfide bonds through exposure of the targeting protein to a reducing agent, such as dithiothreitol.

The free hydrazide group of the targeting protein-linker molecule may then be reacted with aldehyde or ketone groups of a diagnostic or therapeutic agent. One technique thorough which aldehyde or ketone groups may be generated on a diagnostic/therapeutic agent is by oxidation of oligosaccharides (in the case of a glycoprotein agent). With certain diagnostic/therapeutic agents, oxidation of the agent may provide additional in vivo benefits. For instance, oxidation of ricin A chain decreases delivery of ricin A to the mammalian liver.

A method for generating aldehyde/ketone groups on a non-carbohydrate-containing agent involves oxidation of methyl groups or primary hydroxyl groups to form aldehydes, or oxidation of secondary hydroxyl groups to form ketones. For example, the secondary hydroxyl group at the 2' position of the macrocyclic ring of verrucarin A may be oxidized to a ketone. Reaction of the targeting protein-linker and oxidized agent may be represented by the following scheme:

$$\text{Tp-L1-N(H)-NH}_2 + O=C(H)\text{-Agent} \longrightarrow \text{Tp-L1-N(H)-N=C(H)-Agent}$$

Alternatively, an aldehyde group may be introduced into a non-carbohydrate-containing diagnostic or therapeutic agent through use of a heterobifunctional linker having a free reactive aldehyde at one end. An example of a heterobifunctional linker useful in this regard is:

$$\text{(maleimide)-N-C}_6\text{H}_4\text{-C(=O)H} \quad \text{Formula 2}$$

which may be obtained by the following reaction scheme:

$$NO_2\text{-C}_6\text{H}_4\text{-CHO} \longrightarrow NO_2\text{-C}_6\text{H}_4\text{-CH(O-)}_2 \longrightarrow NH_2\text{-C}_6\text{H}_4\text{-CH(O-)}_2 \longrightarrow \text{(maleimide)-N-C}_6\text{H}_4\text{-CH(O-)}_2 \longrightarrow \text{(maleimide)-N-C}_6\text{H}_4\text{-C(=O)H}$$

The maleimide group of this heterobifunctional linker reacts with native sulfhydryl groups on the diagnostic or therapeutic agent (generated through treatment with a reducing agent) or with a sulfhydryl-derivatized agent (iminothiolane-generated sulfhydryls from native lysines of the agent).

The free hydrazide group of the targeting protein-linker molecule is then reacted with the aldehyde group of the agent-linker molecule, forming a stabilized unique Schiff base-linked targeting protein conjugate. This reaction is schematically illustrated below:

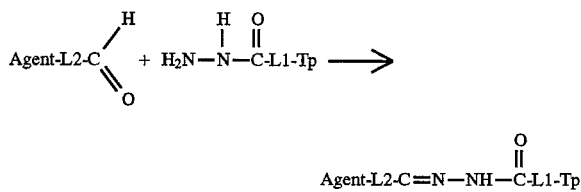

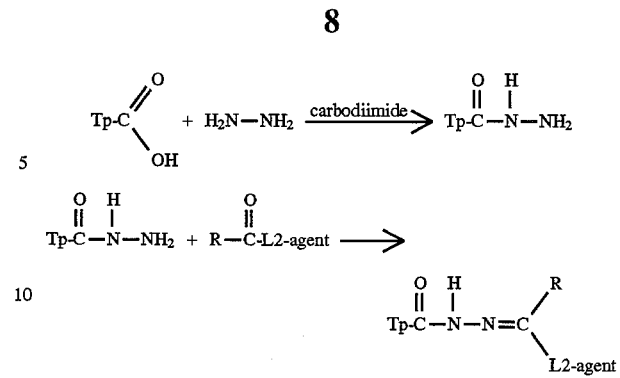

Another heterobifunctional linker useful in this regard has a free reactive aldehyde at one end and an N-hydroxysuccinimide ester at the other end. An exemplary linker in this regard includes:

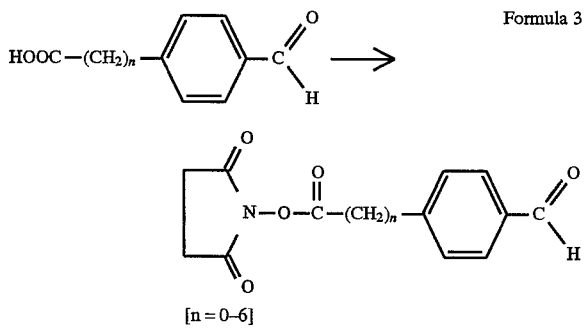

Formula 3

[n = 0–6]

Lysines of the diagnostic or therapeutic agent react with the N-hydroxysuccinimide ester of the linker molecule. The free hydrazide group of the targeting protein is then reacted with the aldehyde group of the agent-linker molecule, as described above.

In a second embodiment of the present invention, a targeting protein is reacted with a heterobifunctional linker having a maleimide reactive group at one end and an aldehyde reactive group at the other end. An example of a heterobifunctional linker useful in this regard has been provided above. The maleimide group of the linker reacts with sulfhydryl groups of a targeting protein (generated as described above).

A diagnostic or therapeutic agent is converted into an agent-hydrazide through reaction with a maleimide hydrazide heterobifunctional linker (as described previously). The free aldehyde group of the targeting protein-linker is then reacted with the diagnostic/therapeutic agent-linker hydrazide, yielding a targeting protein conjugate according to the following scheme:

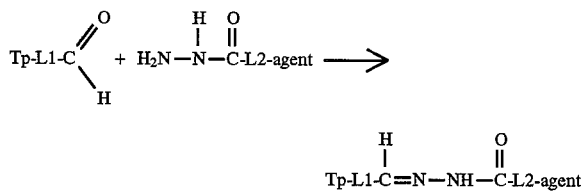

In a third embodiment of the first aspect of the present invention, carboxylic acid groups of a targeting protein are directly derivatized with hydrazine in the presence of carbodiimide to form a targeting protein hydrazide. The targeting protein hydrazide is then covalently attached through a stabilized unique Schiff base linkage to an aldehyde or ketone group present on a diagnostic or therapeutic agent. The following reaction scheme illustrates production of the resultant stabilized unique Schiff base-linked targeting protein conjugate:

A variety of carbodiimides may be used as catalysts in the above reaction scheme, but 1-ethyl-3(3-dimethylaminopropyl)carbodiimide is a particularly preferred carbodiimide.

As depicted in the above reaction scheme, an aldehyde group may be introduced into either a carbohydrate- or non-carbohydrate-containing diagnostic or therapeutic agent through use of a heterobifunctional linker having a free reactive aldehyde at one end. In this illustrative example, L2 is present (n=1). Alternatively, aldehyde or ketone group(s) on the diagnostic/therapeutic agent may be obtained directly by oxidation of oligosaccharides (in the case of a glycoprotein agent) or oxidation of methyl or secondary hydroxyl groups. When oxidation is used to generate aldehyde/ketone groups on the agent, L2 is not present (n=0).

Crosslinking of targeting protein during reaction with hydrazine is minimized by maintaining the concentration of targeting protein at approximately 2 mg/ml, and by using an excess of hydrazine reactant.

A comparison of the Schiff base-linked conjugates of the first aspect of the claimed invention and known Schiff base-linked conjugates highlights the following advantages provided by the conjugates described herein: (1) Neither the targeting protein nor the diagnostic or therapeutic agent need be a glycoprotein. (2) If the targeting protein and/or the diagnostic or therapeutic agent component of the conjugate is a glycoprotein, this glycoprotein component need not be subjected to harsh oxidizing conditions in order to generate a Schiff base-linked conjugate. This is in contrast to previously described Schiff base-linked conjugates, which require generation of oxidized carbohydrate moieties. (3) Either sulfhydryl, ε-amino or carboxylic acid groups of the targeting protein may be derivatized to in readiness for unique Schiff base-linkage of the agent. (4) In contrast to previously described Schiff base-linked conjugates which require oxidized oligosaccharide moieties, the degree of conjugation of the targeting protein or diagnostic or therapeutic agent of the present invention may be controlled (for instance, through the amount of hydrazide or linker substituted onto the targeting protein and/or agent components). Where Schiff base-linked conjugates are obtained using oxidized oligosaccharides, the degree of conjugation is directly related to the amount of carbohydrate natively associated with the glycoprotein. (5) Stabilized Schiff base conjugates of the claimed invention need not be subjected to reducing conditions in order to stabilize a Schiff base (imine) bond.

A second aspect of the present invention involves a targeting protein-diagnostic/therapeutic agent conjugate joined through a heterobifunctional, aromatic Schiff base linker. In a first embodiment of this aspect of the invention, a targeting protein conjugate has the following formula:

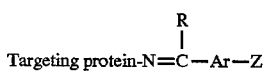

wherein
- "Ar" is a substituted or unsubstituted aryl group derived from an aromatic aldehyde or ketone having the formula R—CO—Ar;
- "N" is a nitrogen atom contributed by the targeting protein;
- "C" is a carbon atom contributed by the aromatic aldehyde or ketone;
- "R" is H or an alkyl, aryl or heteroaryl substituent contributed by the aromatic aldehyde or ketone; and
- "Z" is a diagnostic or therapeutic agent attached either directly or indirectly to Ar.

Preferred Ar groups in this regard include monocyclic aromatic rings, annulated aromatic rings, carbocyclic aromatic rings and heterocyclic ring systems. Particularly preferred Ar groups include substituted and unsubstituted benzene, furan, pyrrole, thiophene, pyridine, oxazole, imidazole, thiazole and annulated derivatives thereof. A preferred annulated Ar contains 2 to 5 rings.

According to this aspect of the claimed invention, aromatic aldehydes or aromatic ketones are designed and synthesized to act as reversible, acid cleavable linkers useful for controlled release of a diagnostic or therapeutic agent from a targeting protein-diagnostic/therapeutic agent conjugate. It is contemplated that the stability of the Schiff base (imine) linkage depicted above may be modified by altering the electron-withdrawing or electron-donating nature of the linker aromatic ring.

Previously, procedures for Schiff base conjugation of a protein and a carbonyl compound required a final reductive step (reductive amination) for stabilization of the resultant imine linkage. Alternatively, in the case of α-hydroxy aldehydes (such as glyceraldehyde) or glucose, the Schiff base would undergo rearrangement to achieve a more stable product (Amadori rearrangement).

In contrast to previously described Schiff base linkages between protein and an aldehyde or ketone compound, the claimed targeting protein conjugate does not require stabilization of the Schiff base linkage (either through reduction or rearrangement). Instead, unreduced imine bond stability is achieved by altering the electron-withdrawing or electron-donating characteristics of the linker aromatic ring substituents. For instance, substitution of ortho-hydroxy groups and/or electron-donating groups on the aromatic ring of the Schiff base linker would increase the lability of the imine bond linkage to acidic conditions. Electron-withdrawing substituents on the aromatic ring of the Schiff base linker would stabilize the imine bond linkage to acidic conditions.

Preferred electron-donating groups in this regard include $O^{31}$, $S^{31}$, $NR'_2$, NHR', $NH_2$, NHCOR', OR', OH, OCOR', SR', SH, Br, I, Cl, F and R'. Preferred electron-withdrawing groups in this regard include $NO_2$, CN, $CO_2H$, $CO_2R'$, $CONH_2$, CONHR', $CONR'_2$, CHO, COR', $SO_2R'$, $SO_2OR'$ and NO. Within the electron-donating and electron-withdrawing groups, R' may be H; a substituted or unsubstituted alkyl, aryl or heteroaryl group; a substituent that increases water solubility of the linker; or a substituent that further affects the stability of the resultant Schiff base linkage.

Within the second aspect of the invention, "Z" indicates a diagnostic or therapeutic agent that is either directly or indirectly attached to Ar. Preferred Z substituents include a directly-linked radionuclide; a functional group suitable for linking a cytotoxic agent; a chelating ligand capable of binding a radiometal; and an organometallic substituent, such as aryltin, that is susceptible to replacement by a radiohalogen.

The Ar group of the linker may be derivatized with a Z substituent prior to covalent linkage of a targeting protein amine group and an aldehyde or ketone moiety present on Ar (generating a unique Schiff base linkage). If Z is a functional group suitable for linking a cytotoxic agent, a chelating ligand capable of binding a radiometal, or an organometallic substituent, the Z substituent may be reacted with a cytotoxic agent, a radiometal or a radiohalogen subsequent to conjugation of Ar—Z and a targeting protein.

Alternatively, the Z substituent of the aromatic linker of the second aspect of the invention may be first reacted with a cytotoxic agent, a radiometal or a radiohalogen, thereby forming an R—CO—Ar—[Z]-diagnostic/therapeutic agent compound. "[Z]" indicates that the prereaction Z substituent may or may not remain after reaction of Z with the diagnostic or therapeutic agent. The R—CO—Ar—[Z]-diagnostic/therapeutic agent compound is then conjugated with a targeting protein via a Schiff base linkage formed between the R—CO—Ar group of the linker and a targeting protein amine group.

Preferred Z functional groups include activated esters (which react with amino groups), maleimides (which bind to sulfhydryl groups) and haloacetamides (which also bind to sulfhydryl groups). In a particularly preferred embodiment, Z is an N-hydroxysuccinimide ester, which possesses electron-withdrawing properties that increase the acid stability of the Schiff base linkage between the targeting protein and the Ar group. In another particularly preferred embodiment, Z is a bromoacetamide group, which has electron-donating characteristics that decrease the acid stability of the Schiff base linkage of the conjugate.

Exemplary bifunctional linkers and their corresponding synthetic routes are shown below:

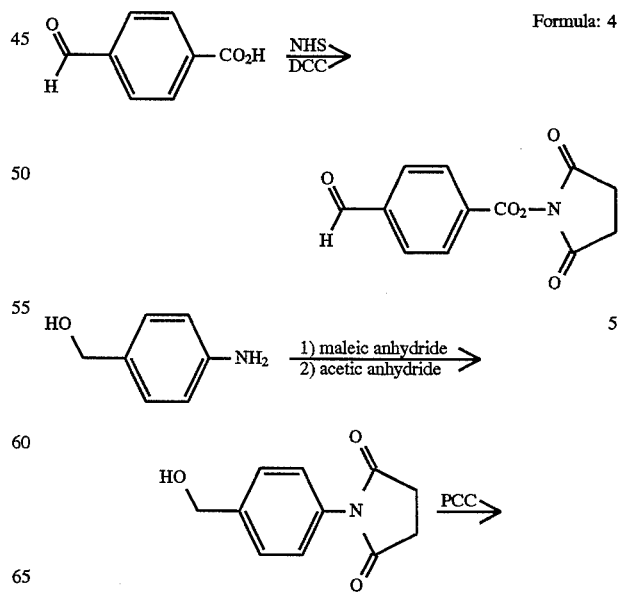

Formula: 4

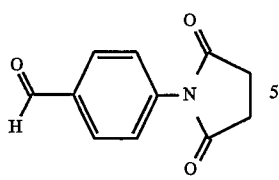

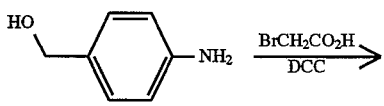

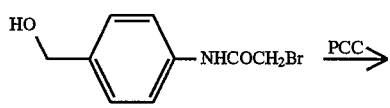

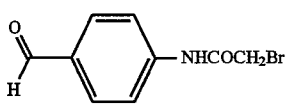

Preferred Z chelating ligands include radionuclide metal chelates as described in Fritzberg, EP 188,256. Particularly preferred chelates in this regard have a free $NH_2$ group capable of reaction with Z when Z is an activated ester or have an available maleimide group capable of reaction with Z when Z is a sulfhydryl. Yet another preferred Z chelating ligand is an aryltin group, as described in Wilbur et al, EP 203,764, with tributyltin particularly preferred. Radiohalogens may then be attached to linker substituent Ar by halodestannylation.

Z may also represent a radionuclide directly attached to the Ar linker substituent, with $^{125}I$ p-iodobenzaldehyde a particularly preferred Ar—Z compound. Appropriately substituted aromatic compounds that have been directly radio-iodinated by addition of electrophilic iodine are also preferred Ar—Z compounds. For instance, the hydroxy group of o-vanillin activates an Ar ring for electrophilic attack by a radiohalogen (i.e., iodine). O-vanillin offers the further advantage of regioselective radiohalogenation, since both Ar ring positions ortho to the activating hydroxy group are occupied (see formula below).

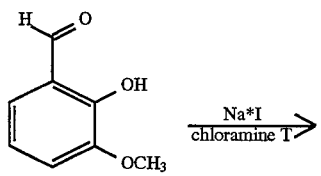

o-vanillin

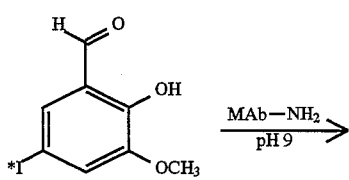

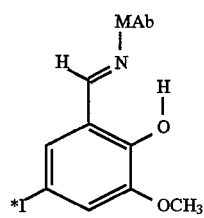

Schiff Base

Preferred diagnostic and therapeutic radionuclides that may be either directly or indirectly attached to Ar include gamma-emitters, positron-emitters, Auger electron-emitters, X-ray emitters and fluorescence-emitters, with beta- or alpha-emitters preferred therapeutic agents. Radionuclides are well-known in the art and include $^{123}I$, $^{125}I$, $^{130}I$, $^{131}I$, $^{133}I$, $^{135}I$, $^{47}Sc$, $^{72}As$, $^{72}Se$, $^{90}Y$, $^{88}Y$, $^{97}Ru$, $^{100}Pd$, $^{101m}Rh$, $^{119}Sb$, $^{128}Ba$, $^{197}Hg$, $^{211}At$, $^{212}Bi$, $^{212}Pb$, $^{109}Pd$, $^{111}In$, $^{67}Ga$, $^{68}Ga$, $^{67}Cu$, $^{75}Br$, $^{76}Br$, $^{77}Br$, $^{99m}Tc$, $^{11}C$, $^{13}N$, $^{15}O$ and $^{18}F$. Preferred therapeutic radionuclides include $^{188}Re$, $^{186}Re$, $^{203}Pb$, $^{212}Pb$, $^{212}Bi$, $^{109}Pd$, $^{64}Cu$, $^{67}Cu$, $^{90}Y$, $^{125}I$, $^{131}I$, $^{77}Br$, $^{211}At$, $^{97}Ru$, $^{105}Rh$, $^{198}Au$ and $^{199}Ag$.

Intracellular release of a cytotoxic agent, a chelating ligand plus agent or a radionuclide from a targeting protein conjugate may be desirable in many instances. In this regard, the claimed diagnostic or therapeutic targeting protein conjugate provides serum stability during delivery of the conjugate to an appropriate target cell. Upon internalization of the conjugate into target cell endosomes, the attached cytotoxic agent or radionuclide is released, which in turn may facilitate translocation of the diagnostic or therapeutic agent or radionuclide from the target cell endosome into the cytoplasm. In the case of certain proteinaceous agents, translocation into the cytoplasm would allow the agent to escape degradation in target cell lysosomes.

Some proportion of administered targeting protein conjugate will bind to normal cells of the mammalian recipient. Typically, if antibody is conjugated to a radiometal using non-cleavable bifunctional linkers, accumulation of significant amounts of radionuclide in normal tissues (i.e., liver and bone marrow) by receptor-mediated endocytosis is observed.

In contrast, the conjugate of the second aspect of the invention provides a reversible (acid-cleavable) attachment of the diagnostic/therapeutic agent to a targeting protein. The claimed conjugate might provide reduced accumulation of the radionuclide in normal tissues, through release of the covalently attached radiometal into the acidic environment of the normal cell endosome/lysosome. As a result, the diagnostic/therapuetic agent (with or without chelator) may be subject to accelerated metabolism and excretion by the normal cell. When the agent is shunted out of the normal cell, it is returned to the bloodstream and rapidly excreted by the kidney, rather than accumulating in normal tissues.

In a second embodiment of the second aspect of the claimed invention, a targeting protein-diagnostic/therapuetic agent conjugate joined by a Schiff base linkage may be synthesized according to the following reaction scheme:

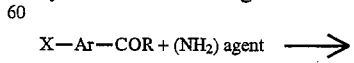

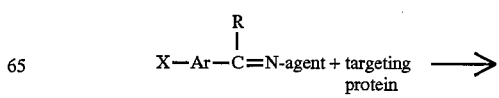

-continued $$\text{targeting protein-X}-\text{Ar}-\overset{\overset{R}{|}}{C}=\text{N-agent}$$

wherein

"X" is $(CH_2)_n$—Y, where n=0–6, Y=active ester, isothiocyanate or maleimide, and X is substituted at the 3 and/or 5 position of Ar;

"Ar" is aryl substituted with electron-donating and/or electron-withdrawing groups at the 2, 4 and/or 6 position;

"R" is H or an alkyl, aryl or heteroaryl substituent contributed by the aromatic aldehyde or ketone; and "agent" is an amino-containing diagnostic or therapeutic agent; an amino-containing chelator for a diagnostic or therapeutic agent; or an amino-containing aromatic organometallic.

In this second embodiment the resultant Schiff base linkage is formed between a diagnostic or therapeutic agent amine and a heterobifunctional, aromatic linker. This is in contrast to the Schiff base linkage in the first embodiment, which is formed between a targeting protein amine and a heterobifunctional, aromatic linker.

The effect of Ar substituents on the formation of Schiff base linkages and on conjugation to a targeting protein should be negligible. However, the rate of hydrolysis of the diagnostic or therapeutic agent from the targeting protein conjugate may be influenced by Ar substituents. For instance, the presence of electron-donating groups at positions 2, 4, and/or 6 of Ar will enhance release of the agent from the conjugate under acidic conditions; the presence of electron-withdrawing groups at positions 2, 4 and/or 6 of Ar will retard or inhibit the release of the agent from the targeting protein conjugate.

Preferred electron-donating groups in this regard include $O^-$, $S^-$, $NR^2$, NHR', $NH_2$, NHCOR', OR', OH, OCOR', SR', SH, Br, I, Cl, F and R'. Preferred electron-withdrawing groups in this regard include $NO_2$, CN, $CO_2H$, $CO_2R'$, $CONH_2$, CONHR', $CONR'_2$, CHO, COR', $SO_2R'$, $SO_2OR'$ and NO. Within the electron-donating and electron-withdrawing groups, R' may be H; a substituted or unsubstituted alky, aryl or heteroaryl group; a substituent that increases water solubility of the linker; or a substituent that further enhances the stability of the resultant Schiff base linkage.

In this embodiment, the targeting protein conjugate is serum stable, but, upon binding at a target cell surface, may be suscepible to thiol addition to the imine (C=N) bond. Thiol addition to the C=N bond of the conjugate would result in hemithioaminal formation (depicted below).

$$\text{Targeting protein-X}-\text{Ar}-\overset{\overset{CH_3}{|}}{\underset{\underset{\text{agent-NH}}{|}}{C}}\sim\overset{\text{S-target cell}}{\underset{\text{membrane protein}}{}}$$

Any effect of Ar substituents on the reaction of the conjugate imine bond with cell surface sulfhydryl groups would be negligible.

Optimal in vivo diagnostic or therapeutic efficacy of targeting protein conjugates may involve three levels of conjugate-target cell membrane interaction: (1) binding of the conjugate to the cell surface membrane; (2) internalization of the conjugate into target cell endosomic vesicles; and (3) translocation of the conjugate from endosomic vesicles into the target cell cytoplasm.

Upon administration of the targeting protein conjugate of this embodiment of the second aspect of the invention, formation of a hemithioaminal would increase retention of the targeting protein conjugate at the cell surface through covalent attachment. Increased retention of the conjugate thus may result in increased internalization and translocation of the conjugate, which in turn may increase the efficacy certain diagnostic/therapeutic agents. For instance, translocation of the conjugate is particularly desirable if the cytotoxic agent component acts on a cytoplasmic target.

To summarize the examples that follow, Example I describes formation of a stabilized unique Schiff base targeting protein (monoclonal antibody) conjugate; Example II discusses a stabilized unique Schiff base conjugate of human serum albumin and 16-oxo-verrucarin A. Synthesis of a targeting protein conjugate joined through an $^{125}I$ benzaldehyde derivative linker is shown in Example III. Production of a targeting protein conjugate joined through a substituted acetophenone linker is described in Example IV.

The following examples are offered by way of illustration, and not by way of limitation.

EXAMPLE I

Formation of Stabilized Unique Schiff Base Targeting Protein Conjugate

A. Using Targeting Protein Sulfhydryls

Formation of a targeting protein hydrazide is achieved by treating monoclonal antibody (MAb; 5 mg/ml in phosphate-buffered saline [PBS], pH 8.5) with 10 mM dithiothreitol (DTT). The reaction mixture is agitated at room temperature for 30 minutes, and the reduced MAb is passed through a PD-10 column (Pharmacia, Uppsala, Sweden) to remove unreacted DTT.

The reduced monoclonal antibody is derivatized with a heterobifunctional linker of Formula 1. Any targeting protein containing one or more native disulfide bonds can thus be converted to a targeting protein hydrazide.

The trichothecene therapeutic agent 16-oxo verrucarin A is prepared by selenium dioxide oxidation of verrucarin A. The MAb hydrazide is then reacted with 16-oxo verrucarin A at 4° C. overnight with agitation, thereby yielding a unique Schiff base-linked targeting protein having the following structure:

$$\text{MAb-L1}-\overset{\overset{O}{\|}}{C}-\overset{\overset{H}{|}}{N}-N=\!=\!=\text{CH-agent}$$

B. Using Targeting Protein Lysines

Monoclonal antibody (5 mg/ml in PBS, pH 8.5) is treated with iminothiolane (IT); the amount of IT offered to the MAb preparation will be dependent on the number of free MAb sulhydryls desired. The reaction of IT with targeting protein lysines is schematically represented as follows:

$$\text{MAB-NH}_2 + \text{H}_2\text{C}\underset{\underset{S}{}}{\overset{H_2C-CH_2}{\diagup\diagdown}}C\overset{+}{=}\text{NH}_2\text{Cl}^-\longrightarrow$$

-continued $$\begin{array}{c} \text{H} \quad \text{NH}_2 \\ | \quad | \\ \text{MAb-N—C—H} \\ | \\ \text{HS—H}_2\text{C—H}_2\text{C—CH}_2 \end{array}$$

The reaction mixture is agitated at room temperature for 30 minutes, then passed through a PD-10 column to remove unreacted IT. The sulfhydryl-derivatized MAb is then reacted with a heterobifunctional linker of Formula 1 to form a MAb hydrazide, as described in Example I.A.

Ricin A chain is oxidized with 10 mM $NaIO_4$, pH 5.5 at room temperature for 1 hour to generate free aldehyde groups from native ricin A oligosaccharide moieties. A significant advantage obtained through unique Schiff base linkage of ricin A aldehyde groups is that oxidation of ricin A decreases the amount of ricin A non-specifically delivered to the mammalian liver (as compared with non-oxidized ricin A).

The oxidized ricin A is then reacted with the MAb hydrazide produced above, yielding a unique Schiff base targeting protein having the following formula:

$$\text{MAb-L1} \begin{array}{c} \text{O} \quad \text{H} \quad \text{H} \\ \| \quad | \quad | \\ \text{—C—N—N}\!\!=\!\!\!=\!\!\text{C-ricin A} \end{array}$$

Iminothiolane-derivatization may be used to generate free sulfhydryls on any lysine-containing protein or peptide. A heterobifunctional linker having a reactive maleimide on one end and a hydrazide group on the other end may then be used to form a proteinaceous hydrazide from a lysine-containing protein or peptide (i.e., regardless of whether the protein or peptide contains native disulfide bonds).

C. Using Targeting Protein Carboxylic Acid Groups

A solution of monoclonal antibody (2 mg/ml in PBS, pH 6.5) is reacted with excess hydrazine (1:150) and 1-ethyl-3 (3-dimethylaminopropyl)-carbodiimide (1:100) and agitated for approximately 1 hour at room temperature to form a hydrazide of the MAb. Reaction conditions (reactant ratios and reaction time) may vary somewhat depending on the monoclonal antibody used. At the end of the 1 hour incubation, the monoclonal antibody hydrazide is passed through a PD-10 column to remove unreacted hydrazine and 1-ethyl-3 (3-dimethylaminopropyl)-carbodiimide.

The reaction described directly introduces hydrazine onto the MAb, without the use of a heterobifunctional linker having a reactive hydrazine group. Dimerization (crosslinking) of MAb is prevented by maintaining a concentration of targeting protein (MAb) of approximately 2 mg/ml, and by using a large excess of hydrazine reactant. Further, the reaction described may be used with any targeting protein that contains one or more free carboxylic acid groups, whether glycoprotein or non-glycoprotein.

EXAMPLE II

Formation of Stabilized Unique Schiff Base Conjugate of Human Serum Albumin and Verrucarin A A solution of human serum albumin (HSA) is reacted with 1-ethyl-3(3-dimethyl-aminopropyl)-carbodiimide as in Example I.C. to form a hydrazide of (HSA) These reaction conditions favor formation of the hydrazide with minimization of HSA crosslinking. The HSA hydrazide is then reacted with 16-oxo-verrucarin A, as described in Example I, to form a conjugate of HSA and 16-oxo-verrucarin A that is joined by a stabilized unique Schiff base linkage.

EXAMPLE III

Synthesis of a Targeting Protein Conjugate Joined Through a $^{125}$I Benzaldehyde Derivative Linker Radiolabeled benzaldehyde linkers demonstrate the relationship between aromatic aldehyde ring substituents and acid-catalyzed hydrolysis of Schiff base-containing radionuclide-targeting protein conjugates.

Briefly, $^{125}$I-p-iodobenzaldehyde was prepared as follows:

The tri-n-butyltin precursor to p-iodobenzaldehyde was prepared from commercially available p-bromobenzyl alcohol (Aldrich Chemical Co., Milwaukee, Wis.). Treatment of the p-bromobenzyl alcohol compound with hexabutylditin and $Pd(PPh_3)_4$ in toluene yielded the desired aryl tin compound. The alcohol was oxidized to the corresponding aldehyde with pyridinium chlorochromate (PCC) in methylene chloride solvent. The product was isolated in 69% yield after silica gel chromatography (ethyl acetate/hexanes) as a pale yellow oil. $^1$H NMR ($CDCl_3$) δ 0.83–1.61 (m, 27H); 7.64 (d, J=8 Hz, 2H); 7.78 (d, J =8 Hz, 2 Hz); 9.98 (s, 1H); $^{13}$C NMR ($CDCl_3$) δ 9.88, 13.82, 27.54, 29.25, 128.99, 129.59, 136.97, 137.50, 193.61.

A trace radiolabeling was accomplished with NCS/$^{125}$I to give the desired product, as evidenced by coinjection with a cold standard. The reaction conditions for labeling were as follows: To a solution of 0.05 mg of the benzaldehyde derivative in 0.05 ml of 1% acetic acid/MeOH was added approximately 360 μCi Na$^{125}$I and 0.0019 mg NaI carrier (1 mg/ml MeOH). To this mixture was added 17 μl of NCS (1 mg/ml in MeOH). After 30 minutes at room temperature, 17 μl of sodium bisulfite solution (0.72 mg/ml in water) was added to quench the reaction. The radiochemical yield obtained was 93%.

Upon conjugation of $^{125}$I-p-iodobenzaldehyde to monoclonal antibody NR-ML-05 (11:1 aldehyde:protein) at pH 9.0, 58% of the offered radiolabeled aldehyde was covalently attached to antibody.

The radionuclide-monoclonal antibody conjugate was purified by centrifugation (5,000 RPM, 10 min, room temperature) through a 30,000 MW microconcentrator (Amicon, Danvers, Mass.), yielding a conjugate of 97% purity by instant thin layer chromatography (ITLC). An analysis of specific activity of the purified conjugate indicated that approximately two lysine residues per antibody molecule had been modified.

Radiolabeled 5-iodo-3-methoxysalicylaldehyde and 5-iodo-3-methylsalicylaldehyde (below) are prepared by radioiodination of o-vanillin and 3-methylsalicyl-aldehyde, respectively.

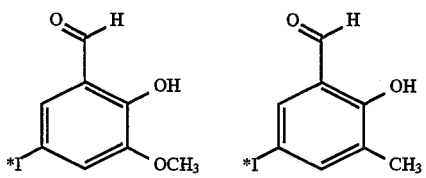

Radioiodination of o-vanillin and 3-methylsalicylaldehyde should be regioselective, since both positions ortho to the hydroxy substituent of the aromatic ring are occupied.

The iodinated aromatic aldehydes illustrated above should demonstrate decreased acid stability as compared to $^{125}$I-p-iodobenzaldehyde, since the ortho-hydroxy substituents can protonate a Schiff base linkage via an intramolecular mechanism. More particularly, the meta methoxy group of 5-iodo-3-methoxysalicylaldehyde has slight electron-withdrawing properties that may increase the acid stability of the Schiff base linkage; the meta methyl group of 3-methylsalicylaldehyde has electron-donating characteristics, which should decrease the stability of the Schiff-base-linked conjugate. Conjugates containing radiolabeled 5-iodo-3-methoxysalicylaldehyde and 5-iodo-3-methylsalicylaldehyde can be characterized as having "stable" conventional Schiff base linkages that are cleavable under mildly acidic conditions (pH 5–6).

EXAMPLE IV

Schiff Base-Linked Targeting Protein Conjugates Joined by a Substituted Acetophenone Linker A stable Schiff base linkage between an amine and an aromatic carbonyl compound is formed using adriamycin and substituted or unsubstituted acetophenone, as shown below:

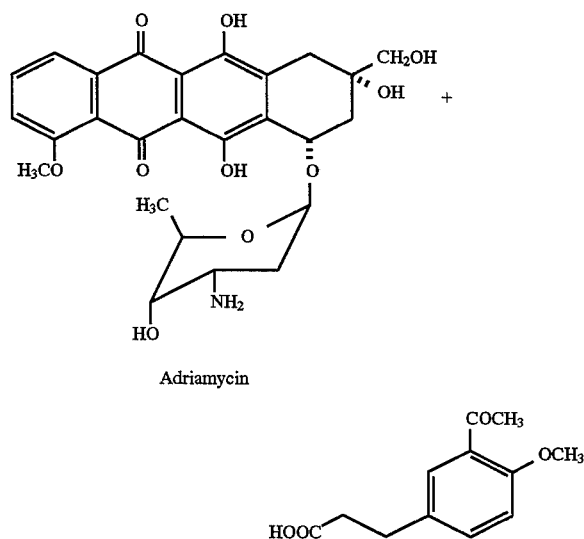

Briefly, formation of a Schiff base linkage is accomplished by briefly refluxing equimolar amounts of adriamycin and substituted acetophenone, or by mixing these reactants in an aprotic solvent in the presence of a dehydrating agent (for instance, a molecular sieve). If the acetophenone is substituted with a —COOH group, the —COOH is converted to an active ester after formation of the Schiff base-linked adriamycin-acetophenone compound. Alternatively, if the acetophenone is substituted with a maleimide group, no further reaction of the acetophenone prior to reaction with targeting protein is necessary.

The Schiff base-linked adriamycin-acetophenone compound is conjugated with monoclonal antibody (MAb) (i.e., intact MAb, F(ab')$_2$ fragment, F(ab') fragment or Fab fragment). If the targeting protein-reactive group of the adriamycin-acetophenone compound is an active ester, the reaction with MAb will preferably be done at pH 8–10. If the targeting protein reactive group of the adriamycin-acetophenone compound is maleimide, the reaction with MAb will preferably be done at pH 6–7. A range of concentrations of adriamycin-acetophenone compound and MAb will be tested in order to determine what concentration of each yields optimal immunoreactivity of the resultant targeting protein conjugate. The optimal concentration of targeting protein reactant required to achieve maximum conjugate immunoreactivity will vary depending on the particular targeting protein to be conjugated (i.e., antibody vs. hormone; one MAb vs. another MAb). The resultant targeting protein-therapeutic agent conjugate may be depicted as follows:

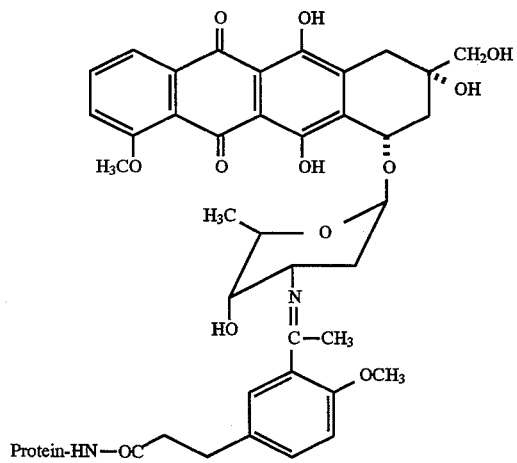

A therapeutically effective amount of the monoclonal antibody-adriamycin Schiff base-linked conjugate is administered intravenously to a tumor-bearing patient. Upon binding of the targeting protein-drug conjugate to an appropriate tumor target cell, thiol groups present at the tumor cell membrane surface may add to the C=N Schiff base imine bond, producing a hemithioaminal (as depicted below).

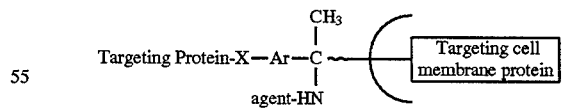

Formation of the hemithioaminal increases retention of the monoclonal antibody-drug conjugate at the tumor cell surface, which in turn may lead to increased tumor cell cytotoxicity.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A targeting protein conjugated to a radionuclide by a Schiff base linker and having the formula:

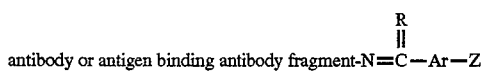

wherein etc.

"Ar" is a substituted or unsubstituted aryl group;

"N" is a nitrogen atom;

"C" is a carbon atom;

"R" is H or an alkyl, aryl or heteroaryl substituent; and

"Z" comprises a radionuclide selected from the group consisting of $^{123}$I, $^{125}$I, $^{130}$I, $^{131}$I, $^{133}$I, $^{135}$I, $^{47}$Sc, $^{72}$Se, $^{90}$Y, $^{88}$Y, $^{97}$Ru, $^{119}$Sb, $^{197}$Hg, $^{211}$At, $^{212}$Bi, $^{212}$Pb, $^{111}$In, $^{67}$Ga, $^{68}$Ga, $^{67}$Cu, $^{75}$Br, $^{76}$Br, $^{99m}$Tc, $^{18}$F, $^{188}$Re, $^{186}$Re, $^{203}$Pb, $^{64}$Cu, $^{105}$Rh, $^{198}$Au and $^{199}$Au, and wherein the substituent of Ar, if present, is an electron-withdrawing group or an electron-donating group capable of modifying unreduced imine bond stability of the Schiff base linker, and wherein the Schiff base is formed by a process which comprises:

reacting a non-oxidized and native amine-bearing or amine-derivatized targeting protein with aromatic aldehyde or ketone, wherein the aromatic aldehyde or ketone is directly conjugated to Z or indirectly conjugated to Z via a chelating ligand, to form a stabilized Schiff base linker, absent a subsequent stabilizing step with respect to the C=N bond, wherein antibody antigen binding antibody fragment carbohydrate content is not determinative of maximum possible aromatic aldehyde or ketone conjugation to the antibody or antigen binding antibody fragment.

2. The antibody or antigen binding antibody fragment conjugate of claim 1 wherein Ar is selected from the group consisting of a monocyclic aromatic ring, an annulated aromatic ring, a carbocyclic aromatic ring and a heterocyclic ring system.

3. The antibody or antigen binding antibody fragment conjugate of claim 2 wherein Ar is selected from the group consisting of substituted and unsubstituted benzene, furan, pyrrole, thiophene, pyridine, oxazole, imidazole, thiazole and annulated derivatives thereof.

4. The antibody or antigen binding antibody fragment conjugate of claim 1 wherein the electron-withdrawing group is selected from the group consisting of $NO_2$, CN, $CO_2H$, $CO_2R'$, $CONH_2$, CONHR', $CONR'_2$, CHO, COR', $SO_2R$, SO2OR' and NO, wherein R' may be H, a substituted or unsubstituted alkyl, aryl or heteroaryl, a substitutent that increases water solubility, or a substituent that affects Schiff base linkage stability.

5. The antibody or antigen binding antibody fragment conjugate of claim 1 wherein the electron-donating group is selected from the group consisting of O$^-$, S$^-$, NR'$_2$, NHR', NH$_2$, NHCOR', OR', OH, OCOR', SR', SH, Br, I, Cl, F and R', wherein R' may be H, a substituted or unsubstituted alkyl, aryl or heteroaryl, a substituent that increases water solubility, or a substituent that affects Schiff base linkage stability.

6. The antibody or antigen binding antibody fragment conjugate of claim 1 wherein Z is a radiohalogen.

7. The antibody or antigen binding antibody fragment conjugate of claim 1 wherein Z comprises $^{99m}$Tc, $^{188}$Re, or $^{186}$Re bound by a chelating ligand.

* * * * *